(12) United States Patent
Friedrich

(10) Patent No.: US 10,588,490 B2
(45) Date of Patent: Mar. 17, 2020

(54) HAND-OPERATED ENDOSCOPE FOR MEDICAL PURPOSES

(71) Applicant: Karl Storz GmbH & Co. KG, Tuttlingen (DE)

(72) Inventor: Markus Friedrich, Rottweil (DE)

(*) Notice: Subject to any disclaimer, the term of this patent is extended or adjusted under 35 U.S.C. 154(b) by 43 days.

(21) Appl. No.: 13/911,823

(22) Filed: Jun. 6, 2013

(65) Prior Publication Data

US 2013/0345503 A1 Dec. 26, 2013

Related U.S. Application Data

(63) Continuation of application No. PCT/DE2011/002025, filed on Nov. 23, 2011.

(30) Foreign Application Priority Data

Dec. 8, 2010 (DE) .................. 10 2010 053 814

(51) Int. Cl.
*A61B 1/00* (2006.01)
*A61B 1/04* (2006.01)
*A61B 1/06* (2006.01)

(52) U.S. Cl.
CPC ...... *A61B 1/00105* (2013.01); *A61B 1/00016* (2013.01); *A61B 1/00018* (2013.01); *A61B 1/00034* (2013.01); *A61B 1/00045* (2013.01); *A61B 1/00103* (2013.01); *A61B 1/00124* (2013.01); *A61B 1/00135* (2013.01); *A61B 1/00142* (2013.01); *A61B 1/04* (2013.01); *A61B 1/0661* (2013.01); *A61B 1/00114* (2013.01)

(58) Field of Classification Search
CPC ............ A61B 1/00071; A61B 1/00121; A61B 1/00124; A61B 1/00128; A61B 1/00142; A61B 1/00135; A61B 1/012; A61B 1/018; A61B 1/12; A61B 1/121; A61B 1/126; A61B 1/127
USPC ....... 600/106, 109, 114, 117, 121, 122, 160, 600/133, 125
See application file for complete search history.

(56) References Cited

U.S. PATENT DOCUMENTS

| | | | | |
|---|---|---|---|---|
| 3,897,775 A | * | 8/1975 | Furihata | ........................ 600/131 |
| 4,878,485 A | | 11/1989 | Adair | |
| 4,895,138 A | * | 1/1990 | Yabe | ........................ A61B 1/05 |
| | | | | 348/E5.027 |
| 5,402,768 A | * | 4/1995 | Adair | ........................... 600/106 |

(Continued)

FOREIGN PATENT DOCUMENTS

| | | | | |
|---|---|---|---|---|
| WO | WO 9315648 A1 | * | 0/0000 | ......... A61B 1/00052 |
| WO | 2006031897 A1 | | 5/2006 | |
| WO | 2008139461 A2 | | 11/2008 | |

OTHER PUBLICATIONS

International Search Report & Written Opinion of the International Searching Authority Application No. PCT/DE2011/002025 Completed: Apr. 20, 2012; dated May 2, 2012 14 pages.

*Primary Examiner* — Timothy J Neal
*Assistant Examiner* — William B Chou
(74) *Attorney, Agent, or Firm* — Whitmyer IP Group LLC

(57) ABSTRACT

A hand operated endoscope for medical purposes, the endoscope including a separate, modular unit consisting of a camera system with an associate lens system, light source and a transmission system. This unsterilized modular unit can be used in a sterilized housing.

13 Claims, 3 Drawing Sheets

(56) References Cited

U.S. PATENT DOCUMENTS

| | | | | |
|---|---|---|---|---|
| 5,487,661 | A | * | 1/1996 | Peithman ............ A61B 1/00142 433/116 |
| 5,496,259 | A | * | 3/1996 | Perkins .................... A61B 1/05 600/121 |
| 5,573,494 | A | * | 11/1996 | Yabe et al. .................... 600/121 |
| 5,609,561 | A | * | 3/1997 | Uehara .................. A61B 1/042 348/75 |
| 6,007,484 | A | * | 12/1999 | Thompson ......... A61B 1/00096 600/122 |
| 6,080,101 | A | * | 6/2000 | Tatsuno et al. ............... 600/112 |
| 6,095,970 | A | * | 8/2000 | Hidaka .............. A61B 1/00124 600/109 |
| 6,790,173 | B2 | * | 9/2004 | Saadat et al. ............ A61B 1/04 600/114 |
| 2004/0111081 | A1 | * | 6/2004 | Whitman et al. .................. 606/1 |
| 2005/0283048 | A1 | * | 12/2005 | Gill et al. ................ A61B 1/00 600/121 |
| 2007/0171013 | A1 | * | 7/2007 | Fujimori et al. ............. 335/151 |
| 2008/0195128 | A1 | * | 8/2008 | Orbay et al. ........... A61B 17/32 606/170 |
| 2010/0204546 | A1 | * | 8/2010 | Hassidov et al. ............. 600/114 |

\* cited by examiner

HAND-OPERATED ENDOSCOPE FOR MEDICAL PURPOSES

FIELD OF THE INVENTION

The invention relates to a hand-operated endoscope for medical purposes.

BACKGROUND OF THE INVENTION

Endoscopes are known in various embodiments. In principle, an endoscope is an instrument that can be used to examine the interior of living organisms (and also of technical cavities). The endoscopes are, in particular, used in human medical diagnostics and for surgery.

The known hand-operated endoscopes for medical purposes are composed of a plurality of individual units. Provision is firstly made for an optical unit with an eyepiece. A light source is connected to this optical unit by means of an optical waveguide. Provision is furthermore made for an image camera or a video camera. This camera is mechanically connected to this optical unit via the eyepiece of the optical unit. Finally, the camera is connected to a camera control unit by an appropriate cable.

A disadvantage of this known hand-operated endoscopy system is that it consists of a plurality of individual units. Together, these are very unwieldy in relation to the practical use of the endoscope. A further—serious—disadvantage lies in the sterilization of the endoscope. The optical and electronic components of the endoscope are very sensitive and subject to increased wear due to the necessary regular sterilizations of the endoscope.

SUMMARY OF THE INVENTION

Proceeding from this, the invention is based on the object of developing an improved hand-operated endoscope for medical purposes in view of convenience and in view of improved sterilization options.

A first advantage of the hand-operated endoscope according to the invention consists of the fact that, therein, this endoscope system unifies systems which could previously only be realized with different individual components and individual units. As a result, a very convenient system emerges from the endoscope according to the invention, which enables new surgical techniques. The basic concept of the endoscope according to the invention consists of a modular design consisting of two main elements. Firstly, provision is made for an—external—housing. Secondly, provision is made for a module-like component which unifies the camera system with associated optical unit, the light source and the transmission system therein. This module-like component is designed in such a way that it is intended and suitable for being removed from the housing as a separate part. For cleaning, disinfection and sterilization purposes, all that is needed is to remove the module-like component from the housing in order subsequently to be able to sterilize the housing on its own, without having to sterilize the module-like component as well. Since the module-like component and the sensitive parts thereof are therefore not sterilized, this results in a significantly longer service life of the overall system. Hence, overall, integration of the camera, optical unit, light source, optical waveguide, camera electronics, power supply and image transmission system components is provided in a compact system. Documentation by video and/or photos is possible without problems. The particular feature therefore lies in the use of a sterilizable, robust external housing, into which the unsterile component consisting of camera, optical unit, light can be introduced under sterile conditions. In so doing, use can be made of a shank/trocar system with integrated rinsing/suction function.

The endoscope according to the invention has a variety of positive effects on surgery technology. It is possible to reduce the cable connections to the image reproduction and the storage unit, and there furthermore is improved illumination by reducing the light-transmission path. Overall, this means less complexity and higher safety during the preparation for surgery. This preparation for surgery entails the housing being removed from the sterile-goods container. The unsterile component is subsequently introduced into the sterile housing. The housing is finally tightly sealed. After surgery, the component can then be removed from the housing again. Hence it is possible to clean the disassembled housing and subject it to surface disinfection and sterilization and finally store it in a sterile-goods container.

In a preferred embodiment, the housing has a lid which can be opened and closed. This lid is therefore part of the housing, which can be sterilized and disinfected together with the housing. Here, the lid sits tightly on the housing. Here, the lid can be pushed on or screwed on or securely locked to the housing in a different manner. In respect of the housing, the lid can be a separate component. However, it can also be connected to the housing, for example by a type of hinge or the like.

In accordance with another embodiment, the housing has a substantially tubular design. The lid is situated on the rear side of the housing. This means that the above-described component is introduced into the housing from the rear.

Another embodiment proposes that a funnel can be placed onto the housing opening for the sterile introduction of the component into the housing. The advantage of this funnel is that the unsterile component does not come into contact with the sterile outside of the housing when it is inserted into the housing. Like the housing and the lid, this funnel is likewise sterilized prior to use.

A further embodiment proposes that the housing has function buttons. This allows the electronic components and further devices of the endoscope to be controlled. Thus, in order to improve the visualization, the image section can be selected by a zoom function directly on the endoscope. It is also possible, if required, to trigger the suction function using one hand by means of a button on the housing.

Still another embodiment proposes that electric contacting of the component with the electronic parts thereof occurs automatically when the component is inserted into the housing. To this end, appropriate contacts and corresponding counter-contacts are provided in the interior of the housing.

The transmission of the image data of the transmission system of the component to the external receiver can, as per yet another embodiment, be achieved by an appropriate cable connector. Here, the cable connector contacts the transmission device of the module-like component. Here, provision can be made for an appropriate plug-in connection. This cable connection can also serve to supply the electronic components in the interior of the housing with power.

The data transmission (image and function data) may also be realized by radio link instead of the data transmission by cable. The advantage consists of thus providing a cable-free, convenient system which enables new surgical techniques.

In the case where the data transmission is brought about by radio link, the component is supplied with power by means of a rechargeable battery. This rechargeable battery is a component of the above-described module-like component.

Finally, the invention may include a position sensor such that it is possible to align the image recorded by the endoscope on the monitor by means of this position sensor.

BRIEF DESCRIPTION OF THE DRAWINGS

Exemplary embodiments of a hand-operated endoscope for medical purposes according to the invention will be described below on the basis of the drawings. In these.

DETAILED DESCRIPTION OF THE INVENTION

Figure 1:
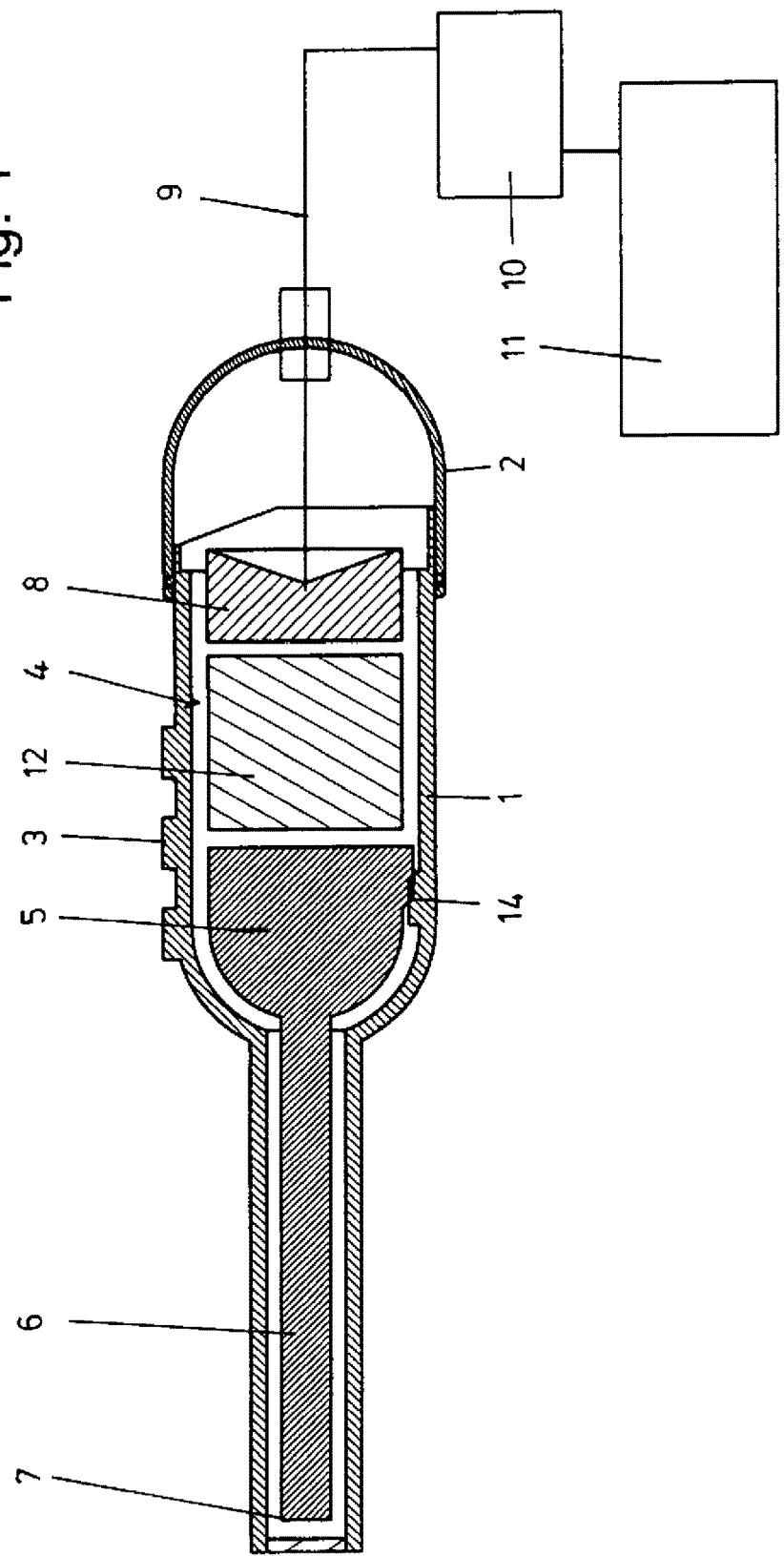
FIG. 1 shows a first variant of the endoscope with a transmission of the data by cable.

The hand-operated endoscope has a substantially tubular housing 1. A rear-side housing opening is tightly sealed by a separate lid 2. The housing 1 furthermore comprises function buttons 3.

A module-like component 4 is provided separately from the housing 1 (with lid 2). This component consists of a digital camera system 5 with optical unit 6 and light source 7. Furthermore, a transmission system 8 is indicated symbolically, which transmission system transmits the obtained image data and the control data to an external receiver 10 via a cable 9. A monitor 11 is connected to this receiver 10.

In FIG. 1, the component 4 additionally comprises rechargeable battery 12. This rechargeable battery 12 could be dispensed with in the case where the power is supplied externally via a power cable.

Figure 3:
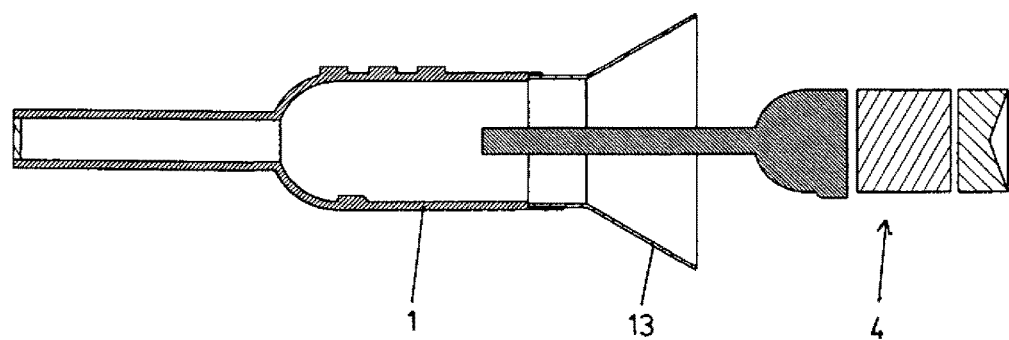
FIGS. 3a to 3c show the assembly of the endoscope in various steps.
Figure 3:
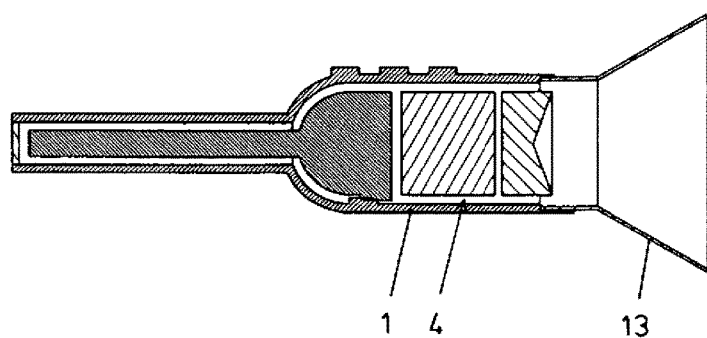
Figure 3:
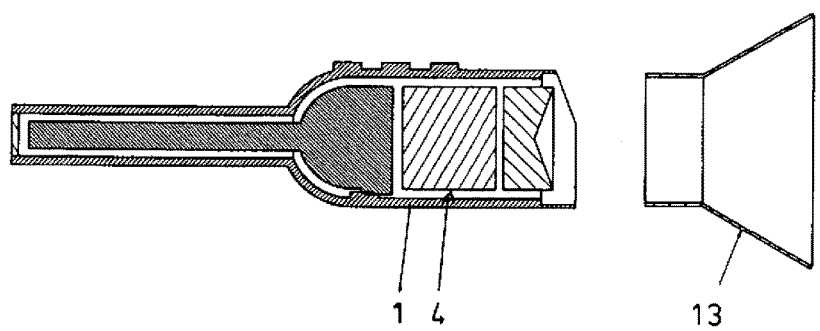

Assembling the endoscope is explained on the basis of FIGS. 3a to 3c:

FIG. 3a shows the sterilized housing 1. A funnel 13, which has likewise been sterilized, is placed onto the rear housing opening. This funnel 13 serves as insertion aid for inserting the unsterile component 4 into the interior of the housing 1.

FIG. 3b shows the situation when the component 4 has been completely inserted into the housing 1. In the process, the component 4 automatically contacts electric contacts 14 of the housing 1. This means that settings can be undertaken by means of the function buttons 3.

FIG. 3c shows the situation when the funnel 13 has been removed from the housing 2 and before, finally, the lid 2 is placed onto the housing 1, as is then depicted in FIG. 1.

Figure 2:
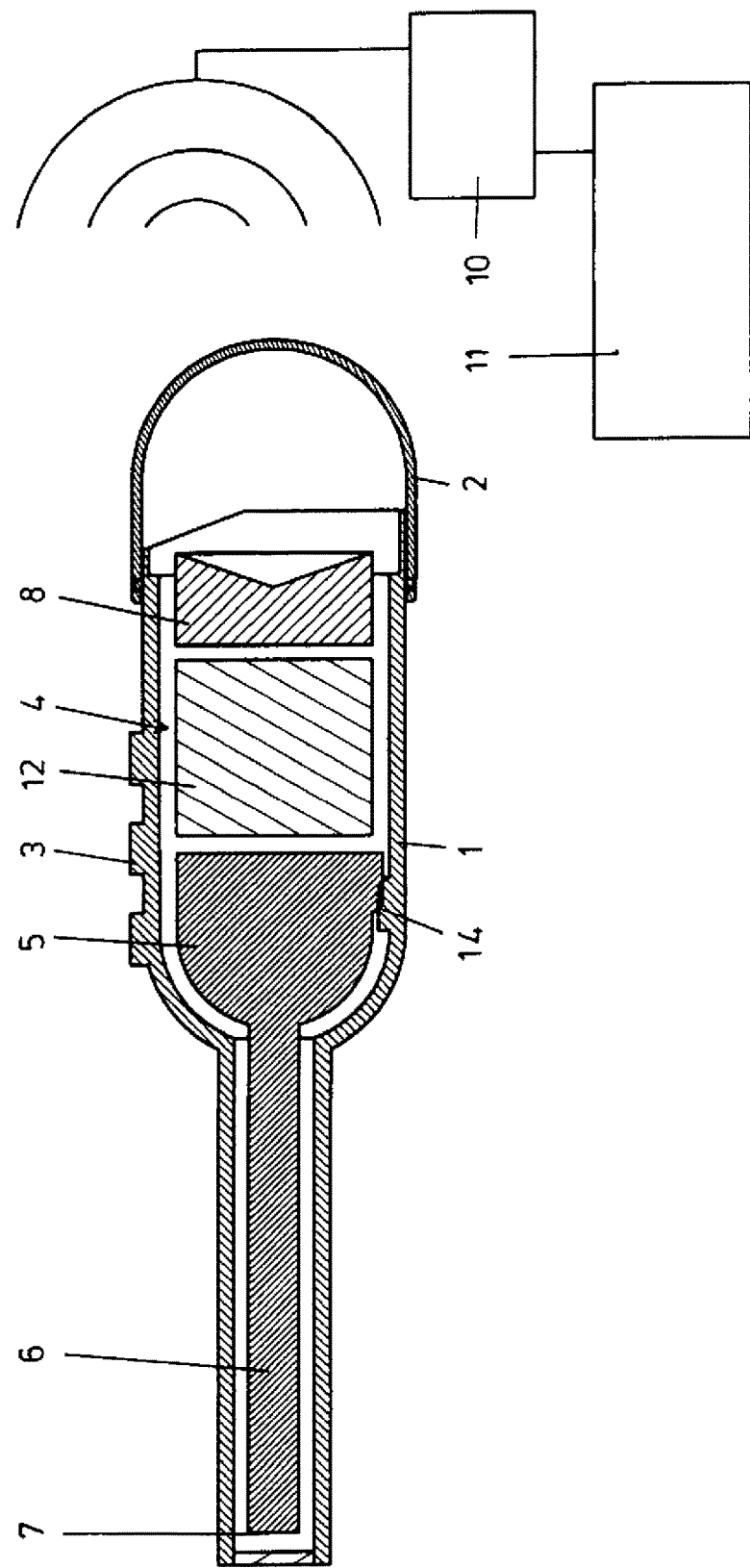
FIG. 2 shows a second variant of the endoscope with a transmission of the data by radio link.

The embodiment variant in FIG. 2 differs from the embodiment variant in FIG. 1 merely in that the data transmission does not take place by a cable 9, but rather that the transmission system 8 enables transmission of the data by radio link to a radio receiver 10. Otherwise this variant does not differ from the variant as illustrated in FIG. 1 and in FIGS. 3a to 3c. However, in this variant in FIG. 2 here, a rechargeable battery 12 is necessarily provided.

The invention claimed is:

1. A hand-operated endoscope for medical purposes, comprising:
   a reusable housing having a lid which is opened and closed via a hinge;
   a digital camera system with associated optical unit;
   a light source; and
   a transmission system configured to transmit image data of the camera system or other data to an external receiver associated with a monitor or another visualization device configured to depict an image on the monitor or another visualization device;
   wherein the digital camera system, the light source, and the transmission system define a removable module component;
   wherein the removable module component is configured to be received entirely within the reusable housing, and is configured to be removed from the reusable housing during separate uses of the hand-operated endoscope;
   wherein the reusable housing is configured to be sterilized after each use of the hand-operated endoscope; and
   wherein the removable module component is unsterilized and is configured to be reintroduced into the reusable housing after the reusable housing has been sterilized.

2. The endoscope of claim 1, wherein the reusable housing has a substantially tubular design, with the lid being situated at a rear end of the reusable housing.

3. The endoscope of claim 1, wherein, when the lid is opened, a tubular part, in particular a funnel, is configured to be placed onto an opening in the reusable housing for subsequent receipt of the removable module component into the reusable housing.

4. The endoscope of claim 1, wherein the reusable housing has function buttons.

5. The endoscope of claim 1, wherein the transmission system is configured to be connected to the external receiver by a cable.

6. The endoscope of claim 1, wherein the transmission system is configured to be connected to the external receiver by radio link.

7. The endoscope of claim 1, wherein the removable module component has a rechargeable battery as power supply.

8. The endoscope of claim 1, wherein the removable module component has a position sensor.

9. The endoscope of claim 1, wherein the removable module component is configured to be received entirely within a single lumen defined by the reusable housing, and is configured to be removed from the single lumen defined by the reusable housing during the separate uses of the hand-operated endoscope.

10. The endoscope of claim 1, wherein the removable module component is configured to be received entirely within the reusable housing as a single unit, and is configured to be removed from the reusable housing as the single unit during the separate uses of the hand-operated endoscope.

11. A hand-operated endoscope for medical purposes, comprising:
   a reusable housing;
   a digital camera system with associated optical unit;
   a light source; and
   a transmission system configured to transmit image data of the camera system or other data to an external receiver associated with a monitor or another visualization device configured to depict an image on the monitor or another visualization device;
   wherein the digital camera system, the light source, and the transmission system define a removable module component;
   wherein the removable module component is configured to be received entirely within the reusable housing, and is configured to be removed from the reusable housing during separate uses of the hand-operated endoscope;

wherein the reusable housing is configured to be sterilized after each use of the hand-operated endoscope; and wherein the removable module component is unsterilized and is configured to be reintroduced into the reusable housing after the reusable housing has been sterilized;

wherein the reusable housing has function buttons;

wherein electric contacts are provided within the reusable housing, the electric contacts are configured to be connected to the function buttons and, when the component is received within the reusable housing, said electric contacts electrically contact corresponding contacts of the removable module component.

12. A hand-operated endoscope for medical purposes, comprising:
  a reusable housing;
  a removable module component arranged entirely in said reusable housing, and configured to be removable from said reusable housing, said removable module component including:
    a digital camera system with associated optical unit;
    a light source; and
    a transmission system for transmitting image data of the digital camera system;
  a funnel for insertion of said removable module component into said reusable housing;
  wherein said reusable housing is sterilized after each use of the hand-operated endoscope; and
  wherein said removable module component arranged in said housing is not sterilized, and
  wherein the removable module component is unsterilized and reintroduced into the reusable housing via said funnel after the reusable housing has been sterilized.

13. The hand-operated endoscope of claim 12, wherein said funnel is sterilized.

* * * * *

UNITED STATES PATENT AND TRADEMARK OFFICE
CERTIFICATE OF CORRECTION

PATENT NO. : 10,588,490 B2
APPLICATION NO. : 13/911823
DATED : March 17, 2020
INVENTOR(S) : Markus Friedrich It is certified that error appears in the above-identified patent and that said Letters Patent is hereby corrected as shown below:

On the Title Page

Item (71), Applicant:
"Karl Storz GmbH & Co. KG, Tuttlingen (DE)"

Should read:
-- Birgit Friedrich, Rottweil (DE)
David Jo Friedrich, Berlin (DE)
Jacob Lloyd Friedrich, Villingendorg (DE) --

Signed and Sealed this
Twenty-sixth Day of May, 2020

Andrei Iancu
*Director of the United States Patent and Trademark Office*